US007868168B2

(12) United States Patent
Patel et al.

(10) Patent No.: US 7,868,168 B2
(45) Date of Patent: Jan. 11, 2011

(54) HIGH VISCOSITY XANTHAN POLYMER PREPARATIONS

(75) Inventors: Yamini Patel, San Diego, CA (US); Jane C. Schneider, San Diego, CA (US); Luis Ielpi, Buenos Aires (AR); Maria Veronica Ielmini, Buenos Aires (AR)

(73) Assignees: C.P. Kelco U.S., Inc., Atlanta, GA (US); Fundacion Instituto Leloir, Buenos Aires (AR)

( * ) Notice: Subject to any disclaimer, the term of this patent is extended or adjusted under 35 U.S.C. 154(b) by 0 days.

(21) Appl. No.: 12/211,170

(22) Filed: Sep. 16, 2008

(65) Prior Publication Data

US 2009/0093626 A1 Apr. 9, 2009

Related U.S. Application Data

(62) Division of application No. 10/802,034, filed on Mar. 17, 2004, now Pat. No. 7,439,044.

(60) Provisional application No. 60/456,245, filed on Mar. 21, 2003.

(51) Int. Cl.
*C07H 1/00* (2006.01)
*C12P 19/06* (2006.01)
*C12N 1/20* (2006.01)
*C12P 21/06* (2006.01)

(52) U.S. Cl. .................. 536/123.1; 435/104; 435/252.3; 435/69.1

(58) Field of Classification Search .............. 536/123.1; 435/104, 252.3, 69.1
See application file for complete search history.

(56) References Cited

U.S. PATENT DOCUMENTS

| 5,854,034 | A | 12/1998 | Pollock et al. |
| 6,391,596 | B1 | 5/2002 | Talashek et al. |
| 7,439,044 | B2 | 10/2008 | Patel et al. |

FOREIGN PATENT DOCUMENTS

WO 87/05938 10/1987

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Seffernick et al., Melamine deaminase and Atrazine chlorohydrolase: 98 percent identical but functionally different. J. Bacteriol.,2001, vol. 183 (8): 2405-2410.*
Vojnov et al., Evidence for a role for the gumB and gumC gene products in the formation of xanthan from its pentasaccharide repeating unit by Xanthomonas campestris. Microbiology, 1998, vol. 144: 1487-1493.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Becker et al., "Xanthan gum biosynthesis and application: a biochemical/genetic perspective," Appl. Microbiol. Biotechnol., 1998, vol. 50, 145-152.
Born et al., "Xanthan," Biopolymers, Wiley-VCH, 259-297.
De Pieri et al., "Overexpression, purification and biochemical characterization of GumC, an enzyme involved in the biosynthesis of exopolysaccharide by X. fastidiosa," Protein Expression and Purification, 2004, vol. 34, 223-228.
Feinbaum, in Current Protocols in Molecular Biology, 1998, by John Wiley & Sons, 1.5.1-1.5.17.
Harding et al., "Genetic and Physical Analyses of a Cluster of Genes Essential for Xanthan Gum Biosynthesis in Xanthomonas campestris," J. Bacteriol., Jun. 1987, 2854-2861.
Harding et al., "Genetics and Biochemistry of Xanthan Gum Production by Xanthomonas campestris," Food Biotech. Microorganisms, 1995, VCH Publishers, Inc., 495-514.
Hassler et al., "Genetic Engineering of Polysaccharide Structure: Production of Variants of Xanthan Gum in Xanthomonas campestris," Biotechnol. Prog., 1990, vol. 6(3), 182-187.
Katzen et al., "Xanthomonas campestris pv. campestris gum mutants: Effects on Xanthan biosynthesis and plant virulence," J. Bacteriol. 1998, vol. 180(7), 1607-1617.
Rao et al., "Imrpovement in Bioreactor Productivities Using Free Radicals: HOCl-Induced Overproduction of Xanthan Gum from X.campestris and Its Mechanism," Biotechnol. Bioeng., 2001, vol. 72(1), 62-68.
Examination Report, European Patent Application No. 04757814.1, mailed Feb. 24, 2010.
Supplementary European Search Report, European Patent Application No. 04757814.1, mailed Aug. 7, 2009.
International Search Report, International Application No. PCT/US04/08302 (WO2004/084814), mailed Aug. 15, 2005.
Hagelin et al., "Structural Analysis of Xanthan," Biocell, Nov. 2003, vol. 27, Suppl. I, 68.

(Continued)

*Primary Examiner*—Ganapathirama Raghu
(74) *Attorney, Agent, or Firm*—Sutherland Asbill & Brennan LLP

(57) ABSTRACT

Increasing the molecular length of xanthan polymer makes a higher viscosity xanthan composition. Xanthan with higher specific viscosity characteristics provides more viscosity at equivalent concentration in food, industrial and oilfield applications. Methods for increasing the viscosity of xanthan include inducing particular key genes and increasing copy number of particular key genes.

7 Claims, 3 Drawing Sheets

OTHER PUBLICATIONS

Kidby et al., "Maintenance Procedures for the Curtailment of Genetic Instability: Xanthomonas campestris NRRL B-1459," Appl. and Environ. Microbiol., 1977, 33(4), 840-845.

Ditta et al., "Plasmids Related to the Broad Host Range Vector, pRK290, Useful for Gene Cloning and for Monitoring Gene Expression," Plasmid, 1985, 13(2), 149-153.

Simon et al., "A Broad Host Range Mobilization System for in vivo Genetic Engineering: Transposon Mutagenesis in Gram-negative Bacteria," Biotechnology, 1983, 1, 784-791.

Katzen et al., "Promoter Analysis of the Xanthomonas campestris pv. campestris Gum Operon Directing Biosynthesis of the Xanthan Polysaccharide," J. Bacteriol., 1996, 178(14), 4313-4318.

Becker et al., "Low-Molecular-Weight Succinoglycan is Predominantly Produced by Rhizobium Meliloti Strains Carrying a Mutated ExoP Protein Characterized by a Periplasmic N-terminal Domain and a Missing C-terminal Domain," Mol. Microbiol., 1995, 16(2), 191-203.

Schafer et al., "Small Mobilizable Multi-Purpose Cloning Vectors Derived from the *Escherichia coli* Plasmids pK18 and pK19: Selection of Defined Deletions in the Chromosome of Corynebacterium Glutamicum," Gene, 1994, 145(1), 69-73.

Yanisch-Perron et al., "Improved M13 Phage Cloning Vectors and Host Strains: Nucleotide Sequences of the M13mp18 and pUC19 Vectors," Gene, 1985, 33(1), 103-119.

Kovach et al., "Four New Derivatives of the Broad-Host-Range Cloning Vector pBBR1MCS, Carrying Different Antibiotic-Cassettes," Gene, 1995, 166(1), 175-176.

Harding et al., "Identification, Genetic and Biochemical Analysis of Genes Involved in Synthesis Sugar Nucleotide Precursors of Xanthan Gum," J. Gen. Microbiol., 1993, 139, 447-457.

* cited by examiner

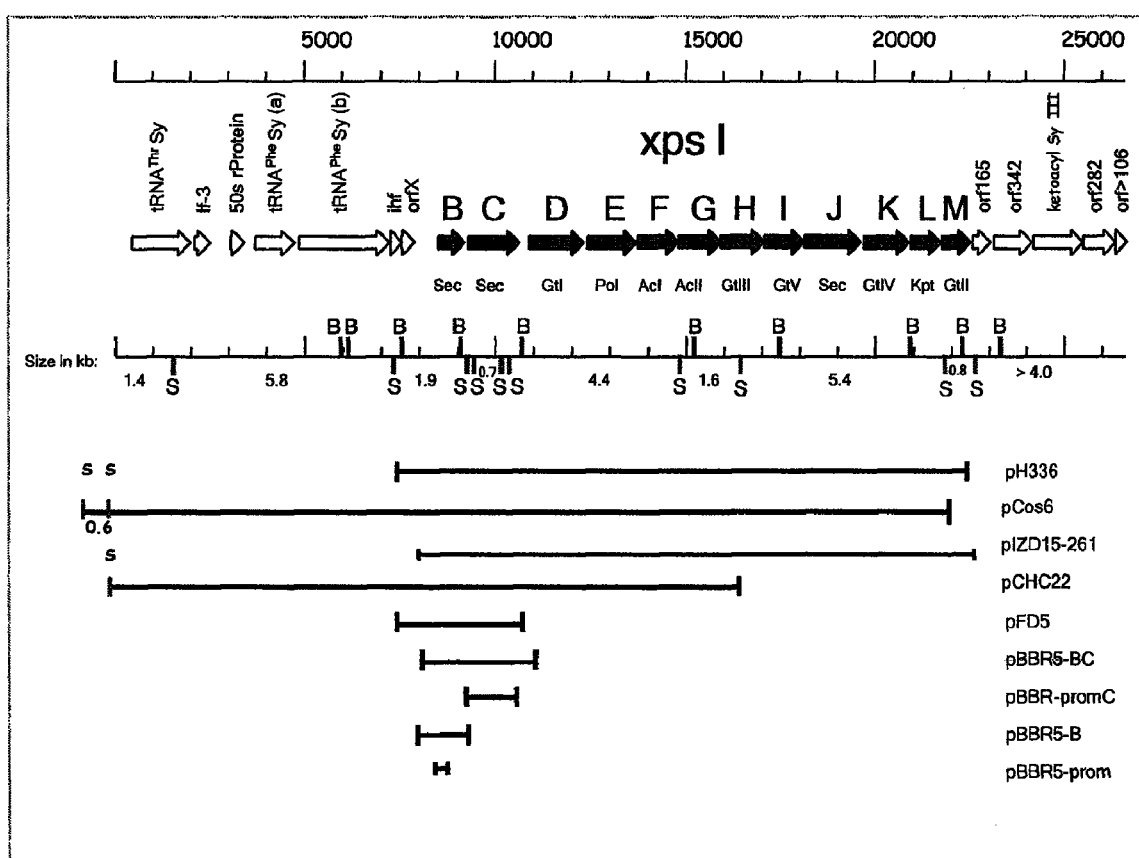
Fig. 1 Xps clones

Fig. 2A Expression level of GumB
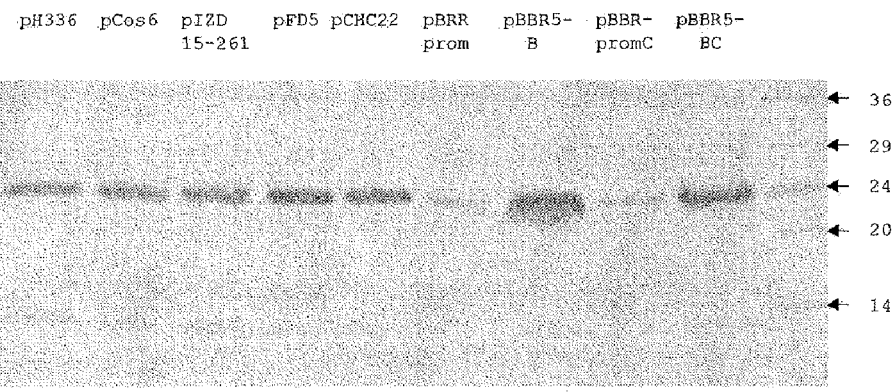
Fig. 2B Expression level of GumC
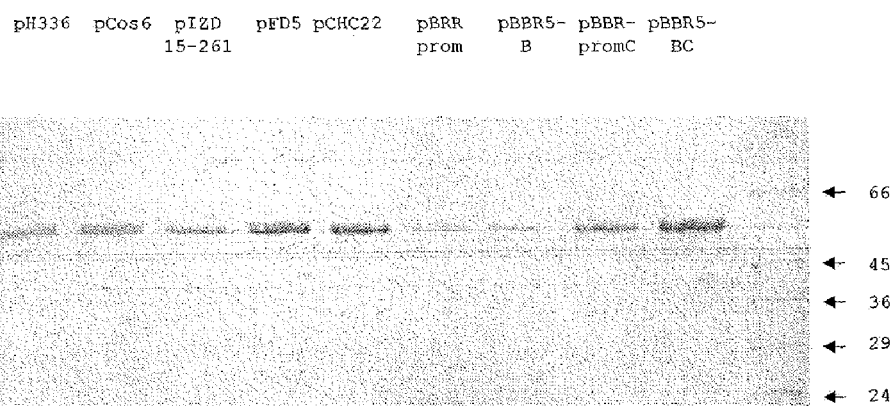

Fig. 3    Intrinsic Viscosity Plot for Xanthan Gum Samples
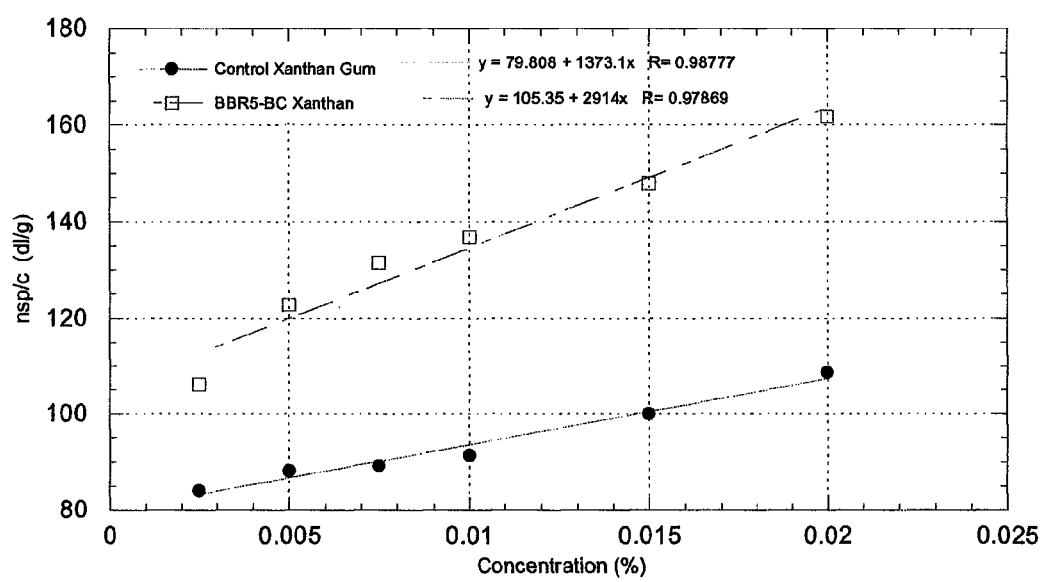

SEQUENCE LISTING

```
<160> NUMBER OF SEQ ID NOS: 5

<210> SEQ ID NO 1
<211> LENGTH: 7604
<212> TYPE: DNA
<213> ORGANISM: Xanthomomas campestris
<220> FEATURE:
<221> NAME/KEY: CDS
<222> LOCATION: (2715)...(4133)
<223> OTHER INFORMATION: gumC
<220> FEATURE:
<221> NAME/KEY: CDS
<222> LOCATION: (2014)...(2712)
```

```
<223> OTHER INFORMATION: gumB
<220> FEATURE:
<221> NAME/KEY: misc_feature
<222> LOCATION: (1915)...(1915)
<223> OTHER INFORMATION: +1
<220> FEATURE:
<221> NAME/KEY: misc_feature
<222> LOCATION: (5812)...(5150)
<223> OTHER INFORMATION: REP (complementary strand)
<220> FEATURE:
<221> NAME/KEY: misc_feature
<222> LOCATION: (794)...(261)
<223> OTHER INFORMATION: genatmicin acetyl transferase (complementary
      strand)
<220> FEATURE:
<221> NAME/KEY: -35_signal
<222> LOCATION: (1840)...(1845)

<400> SEQUENCE: 1
accttcggga gcgcctgaag cccgttctgg acgccctggg gccgttgaat cgggatatgc      60
aggccaaggc cgccgcgatc atcaaggccg tgggcgaaaa gctgctgacg gaacagcggg     120
aagtccagcg ccagaaacag gcccagcgcc agcaggaacg cgggcgcgca catttccccg     180
aaaagtgcca cctggcggcg ttgtgacaat ttaccgaaca actccgcggc cgggaagccg     240
atctcggctt gaacgaattg ttaggtggcg gtacttgggt cgatatcaaa gtgcatcact     300
tcttcccgta tgcccaactt tgtatagaga gccactgcgg gatcgtcacc gtaatctgct     360
tgcacgtaga tcacataagc accaagcgcg ttggcctcat gcttgaggag attgatgagc     420
gcggtggcaa tgccctgcct ccggtgctcg ccggagactg cgagatcata gatatagatc     480
tcactacgcg gctgctcaaa cctgggcaga acgtaagccg cgagagcgcc aacaaccgct     540
tcttggtcga aggcagcaag cgcgatgaat gtcttactac ggagcaagtt cccgaggtaa     600
tcggagtccg gctgatgttg ggagtaggtg gctacgtctc cgaactcacg accgaaaaga     660
tcaagagcag cccgcatgga tttgacttgg tcagggccga gcctacatgt gcgaatgatg     720
cccatacttg agccacctaa ctttgtttta gggcgactgc cctgctgcgt aacatcgttg     780
ctgctgcgta acatcgttgc tgctccataa catcaaacat cgacccacgg cgtaacgcgc     840
ttgctgcttg gatgcccgag gcatagactg tacaaaaaaa cagtcataac aagccatgaa     900
aaccgccact cgcgccgttac caccgctgcg ttcggtcaag gttctggacc agttgcgtga     960
gcgcatacgc tacttgcatt acagtttacg aaccgaacag gcttatgtca actgggttcg    1020
tgccttcatc cgtttccacg gtgtgcgtcc atgggcaaat attatacgca aggcgacaag    1080
gtgctgatgc cgctggcgat tcaggttcat catgccgttt tgatggcttc catgtcggc    1140 agaatgctta atgaattaca acagttttta tgcatgcgcc caatacgcaa accgcctctc    1200
cccgcgcgtt ggccgattca ttaatgcagc tggcacgaca ggtttcccga ctggaaagcg    1260
ggcagtgagc gcaacgcaat taatgtgagt tagctcactc attaggcacc ccaggcttta    1320
cactttatgc ttccggctcg tatgttgtgt ggaattgtga gcggataaca atttcacaca    1380
ggaaacagct atgaccatga ttacgccaag cgcgcaatta ccctcactaa agggaacaa    1440 aagctgggta ccgggccccc cctcgaggtc gacggtatcg ataagcttgc atgcctgcag    1500
gtcgactcta gtggtcgtcg gttcgaatcc ggctaccccg accaaacaac aggcctacgt    1560
cgcaagacgt gggccttttt gttgcgtcgc aacatgtcag ttcgatggca ttccaggcta    1620
tgccactatg cgcaacggca tattgcaagg cggcatatgc aagtcctgta cgcaattatt    1680
tcgcggttca ggctgctaca agtcgggatc agcaggcgtc cgtaagtgcc cggaaacgct    1740
agagttcgta tgctgagaat gacgacccag gtcacgttct cttaacgtcg aggcgacgaa    1800
```

```
cttgaatcaa taggccaacg ccgtcaaaaa aatggcgtgt tgtgccttgc gatgtgttcg    1860
ttctatgcca tagtgcactg caacacgcga ttcaacgttg gtcccggcac gcgtcgggat    1920
gcaacttcct gtcgtacgtt cgtgctggcg cctgagccgg ttgaatgctg cgcgaggtcc    1980
tgtcccaccc aacagaggca gccagctaca cgc atg aag aaa ctg atc gga cga    2034
                                   Met Lys Lys Leu Ile Gly Arg
                                    1               5 ctc tgc caa ggc ctc agc ctg gct ctg ctc tgc tcg atg tcg ctg ggc    2082
Leu Cys Gln Gly Leu Ser Leu Ala Leu Leu Cys Ser Met Ser Leu Gly
         10              15                  20 gct tgc agc acc ggc ccg gag atg gcg tct tcg ctg ccg cat ccg gac    2130
Ala Cys Ser Thr Gly Pro Glu Met Ala Ser Ser Leu Pro His Pro Asp
     25                  30                  35 ccg ctg gca atg tcc acg gtg cag ccc gaa tac cgt ctt gcg ccg ggc    2178
Pro Leu Ala Met Ser Thr Val Gln Pro Glu Tyr Arg Leu Ala Pro Gly
 40                  45                  50                  55 gat ctg ttg ctg gtg aag gtg ttt cag atc gac gat ctg gag cgg cag    2226
Asp Leu Leu Leu Val Lys Val Phe Gln Ile Asp Asp Leu Glu Arg Gln
                 60                  65                  70 gtc cgc atc gac cag aac ggt cac atc tca ctg ccg ttg att ggc gac    2274
Val Arg Ile Asp Gln Asn Gly His Ile Ser Leu Pro Leu Ile Gly Asp
             75                  80                  85 gtc aag gcc gcc ggt ctg ggc gtt ggc gaa ctg gaa aag ctg gtc gcc    2322
Val Lys Ala Ala Gly Leu Gly Val Gly Glu Leu Glu Lys Leu Val Ala
         90                  95                 100 gat cgg tat cgc gca ggc tac ctg cag cag ccg cag att tcg gta ttc    2370
Asp Arg Tyr Arg Ala Gly Tyr Leu Gln Gln Pro Gln Ile Ser Val Phe
    105                 110                 115 gtg cag gag tcc aac ggg cgt cgc gtc acg gtc act ggt gcg gta gac    2418
Val Gln Glu Ser Asn Gly Arg Arg Val Thr Val Thr Gly Ala Val Asp
120                 125                 130                 135 gag ccg ggc atc tac ccg gtg atc ggc gcc aac ctc acc ttg cag cag    2466
Glu Pro Gly Ile Tyr Pro Val Ile Gly Ala Asn Leu Thr Leu Gln Gln
                140                 145                 150 gcg atc gcg cag gcc aag ggt gtc agc acg gtg gca agc cgc ggc aac    2514
Ala Ile Ala Gln Ala Lys Gly Val Ser Thr Val Ala Ser Arg Gly Asn
            155                 160                 165 gtg atc gtg ttc cgc atg gtc aac ggg caa aaa atg att gcg cgg ttc    2562
Val Ile Val Phe Arg Met Val Asn Gly Gln Lys Met Ile Ala Arg Phe
        170                 175                 180 gac ctg acc gag atc gag aag ggg gcc aat ccg gat cct gag att tat    2610
Asp Leu Thr Glu Ile Glu Lys Gly Ala Asn Pro Asp Pro Glu Ile Tyr
    185                 190                 195 ggc ggc gac att gtc gtg gtg tat cgc tcg gat gcg cgc gtg tgg ttg    2658
Gly Gly Asp Ile Val Val Val Tyr Arg Ser Asp Ala Arg Val Trp Leu
200                 205                 210                 215 cgc acc atg ctg gaa ctg acc ccc ttg gtg atg gtg tgg cgc gct tac    2706
Arg Thr Met Leu Glu Leu Thr Pro Leu Val Met Val Trp Arg Ala Tyr
                220                 225                 230 cga tga gt atg aat tca gac aat cgt tcc tct tcg tcg cag cgt cat    2753
Arg  *    Met Asn Ser Asp Asn Arg Ser Ser Ser Ser Gln Arg His
              235                 240                 245 ggt cat ctg gaa ctg gca gat gtc gac ttg atg gac tac tgg cgc gcc    2801
Gly His Leu Glu Leu Ala Asp Val Asp Leu Met Asp Tyr Trp Arg Ala
            250                 255                 260 ctg gtc tcg cag ctc tgg ctg atc atc ctg atc gcc gtc ggc gcg ctg    2849
Leu Val Ser Gln Leu Trp Leu Ile Ile Leu Ile Ala Val Gly Ala Leu
        265                 270                 275
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ttg | ctg | gca | ttc | ggc | atc | acg | atg | ttg | atg | ccc | gag | aag | tac | cgc | gcc | 2897 |
| Leu | Leu | Ala | Phe | Gly | Ile | Thr | Met | Leu | Met | Pro | Glu | Lys | Tyr | Arg | Ala |      |
|     |     | 280 |     |     |     |     | 285 |     |     |     |     | 290 |     |     |     |      |

| acc | agc | acc | ctg | cag | atc | gaa | cgt | gac | tcg | ctc | aat | gtg | gtg | aac | gtc | 2945 |
| --- | --- | --- | --- | --- | --- | --- | --- | --- | --- | --- | --- | --- | --- | --- | --- | ---- |
| Thr | Ser | Thr | Leu | Gln | Ile | Glu | Arg | Asp | Ser | Leu | Asn | Val | Val | Asn | Val |      |
|     | 295 |     |     |     |     | 300 |     |     |     |     | 305 |     |     |     |     |      |

| gac | aac | ctg | atg | ccg | gtg | gaa | tcg | ccg | cag | gat | cgc | gat | ttc | tac | cag | 2993 |
| --- | --- | --- | --- | --- | --- | --- | --- | --- | --- | --- | --- | --- | --- | --- | --- | ---- |
| Asp | Asn | Leu | Met | Pro | Val | Glu | Ser | Pro | Gln | Asp | Arg | Asp | Phe | Tyr | Gln |      |
| 310 |     |     |     |     | 315 |     |     |     |     | 320 |     |     |     |     | 325 |      |

| acc | cag | tac | cag | ttg | ctg | cag | agc | cgt | tcg | ctg | gcg | cgt | gcg | gtg | atc | 3041 |
| --- | --- | --- | --- | --- | --- | --- | --- | --- | --- | --- | --- | --- | --- | --- | --- | ---- |
| Thr | Gln | Tyr | Gln | Leu | Leu | Gln | Ser | Arg | Ser | Leu | Ala | Arg | Ala | Val | Ile |      |
|     |     |     |     | 330 |     |     |     |     | 335 |     |     |     |     | 340 |     |      |

| cgg | gaa | gcc | aag | ctc | gat | cag | gag | ccg | gcg | ttc | aag | gag | cag | gtg | gag | 3089 |
| --- | --- | --- | --- | --- | --- | --- | --- | --- | --- | --- | --- | --- | --- | --- | --- | ---- |
| Arg | Glu | Ala | Lys | Leu | Asp | Gln | Glu | Pro | Ala | Phe | Lys | Glu | Gln | Val | Glu |      |
|     |     |     | 345 |     |     |     |     | 350 |     |     |     |     | 355 |     |     |      |

| gag | gcg | ctg | gcc | aaa | gcc | gcc | gaa | aag | aat | ccc | gag | gcg | ggt | aag | tcg | 3137 |
| --- | --- | --- | --- | --- | --- | --- | --- | --- | --- | --- | --- | --- | --- | --- | --- | ---- |
| Glu | Ala | Leu | Ala | Lys | Ala | Ala | Glu | Lys | Asn | Pro | Glu | Ala | Gly | Lys | Ser |      |
|     |     | 360 |     |     |     |     | 365 |     |     |     |     | 370 |     |     |     |      |

| ctc | gat | tcg | cgg | cag | gcg | atc | gtc | gag | cgc | agc | ctc | acc | gat | acg | ttg | 3185 |
| --- | --- | --- | --- | --- | --- | --- | --- | --- | --- | --- | --- | --- | --- | --- | --- | ---- |
| Leu | Asp | Ser | Arg | Gln | Ala | Ile | Val | Glu | Arg | Ser | Leu | Thr | Asp | Thr | Leu |      |
|     | 375 |     |     |     |     | 380 |     |     |     |     | 385 |     |     |     |     |      |

| ctc | gcc | ggg | ctg | gtg | gtc | gag | ccg | atc | ctc | aac | tcg | cgc | ctg | gtg | tac | 3233 |
| --- | --- | --- | --- | --- | --- | --- | --- | --- | --- | --- | --- | --- | --- | --- | --- | ---- |
| Leu | Ala | Gly | Leu | Val | Val | Glu | Pro | Ile | Leu | Asn | Ser | Arg | Leu | Val | Tyr |      |
| 390 |     |     |     |     | 395 |     |     |     |     | 400 |     |     |     |     | 405 |      |

| gtc | aat | tac | gat | tcg | cca | gac | ccg | gtg | ctg | gcc | gcc | aag | atc | gcc | aat | 3281 |
| --- | --- | --- | --- | --- | --- | --- | --- | --- | --- | --- | --- | --- | --- | --- | --- | ---- |
| Val | Asn | Tyr | Asp | Ser | Pro | Asp | Pro | Val | Leu | Ala | Ala | Lys | Ile | Ala | Asn |      |
|     |     |     |     || 410 |     |     |     |     | 415 |     |     |     |     | 420 |     |      |

| acg | tac | ccg | aag | gtg | ttc | atc | gtc | agc | acc | cag | gaa | cgc | cgc | atg | aag | 3329 |
| --- | --- | --- | --- | --- | --- | --- | --- | --- | --- | --- | --- | --- | --- | --- | --- | ---- |
| Thr | Tyr | Pro | Lys | Val | Phe | Ile | Val | Ser | Thr | Gln | Glu | Arg | Arg | Met | Lys |      |
|     |     |     | 425 |     |     |     |     | 430 |     |     |     |     | 435 |     |     |      |

| gcg | tct | tcg | ttt | gcg | aca | cag | ttt | ctg | gct | gag | cgc | ctg | aag | cag | ttg | 3377 |
| --- | --- | --- | --- | --- | --- | --- | --- | --- | --- | --- | --- | --- | --- | --- | --- | ---- |
| Ala | Ser | Ser | Phe | Ala | Thr | Gln | Phe | Leu | Ala | Glu | Arg | Leu | Lys | Gln | Leu |      |
|     |     |     | 440 |     |     |     |     | 445 |     |     |     |     | 450 |     |     |      |

| cgc | gag | aag | gtc | gaa | gac | tct | gaa | aag | gat | ctg | gtc | tcg | tat | tcg | acc | 3425 |
| --- | --- | --- | --- | --- | --- | --- | --- | --- | --- | --- | --- | --- | --- | --- | --- | ---- |
| Arg | Glu | Lys | Val | Glu | Asp | Ser | Glu | Lys | Asp | Leu | Val | Ser | Tyr | Ser | Thr |      |
|     |     | 455 |     |     |     |     | 460 |     |     |     |     | 465 |     |     |     |      |

| gaa | gag | cag | atc | gtg | tcg | gtt | ggc | gat | gac | aag | ccc | tcg | ctg | cct | gcg | 3473 |
| --- | --- | --- | --- | --- | --- | --- | --- | --- | --- | --- | --- | --- | --- | --- | --- | ---- |
| Glu | Glu | Gln | Ile | Val | Ser | Val | Gly | Asp | Asp | Lys | Pro | Ser | Leu | Pro | Ala |      |
| 470 |     |     |     |     | 475 |     |     |     |     | 480 |     |     |     |     | 485 |      |

| cag | aat | ctg | acc | gat | ctc | aat | gcg | ttg | ctg | gca | tcc | gca | cag | gac | gcc | 3521 |
| --- | --- | --- | --- | --- | --- | --- | --- | --- | --- | --- | --- | --- | --- | --- | --- | ---- |
| Gln | Asn | Leu | Thr | Asp | Leu | Asn | Ala | Leu | Leu | Ala | Ser | Ala | Gln | Asp | Ala |      |
|     |     |     |     | 490 |     |     |     |     | 495 |     |     |     |     | 500 |     |      |

| cgg | atc | aag | gcc | gag | tca | gct | tgg | cgg | cag | gct | tcc | agt | ggc | gat | ggc | 3569 |
| --- | --- | --- | --- | --- | --- | --- | --- | --- | --- | --- | --- | --- | --- | --- | --- | ---- |
| Arg | Ile | Lys | Ala | Glu | Ser | Ala | Trp | Arg | Gln | Ala | Ser | Ser | Gly | Asp | Gly |      |
|     |     |     | 505 |     |     |     |     | 510 |     |     |     |     | 515 |     |     |      |

| atg | tca | ttg | ccg | cag | gtg | ttg | agc | agc | ccg | ctg | att | caa | agc | ctg | cgc | 3617 |
| --- | --- | --- | --- | --- | --- | --- | --- | --- | --- | --- | --- | --- | --- | --- | --- | ---- |
| Met | Ser | Leu | Pro | Gln | Val | Leu | Ser | Ser | Pro | Leu | Ile | Gln | Ser | Leu | Arg |      |
|     |     | 520 |     |     |     |     | 525 |     |     |     |     | 530 |     |     |     |      |

| agc | gag | cag | gtg | cgt | ctg | acc | agc | gag | tac | cag | cag | aaa | ctg | tcg | acc | 3665 |
| --- | --- | --- | --- | --- | --- | --- | --- | --- | --- | --- | --- | --- | --- | --- | --- | ---- |
| Ser | Glu | Gln | Val | Arg | Leu | Thr | Ser | Glu | Tyr | Gln | Gln | Lys | Leu | Ser | Thr |      |
|     | 535 |     |     |     |     | 540 |     |     |     |     | 545 |     |     |     |     |      |

| ttc | aag | ccg | gat | tac | ccg | gag | atg | cag | cgc | ctc | aag | gcg | cag | atc | gaa | 3713 |
| --- | --- | --- | --- | --- | --- | --- | --- | --- | --- | --- | --- | --- | --- | --- | --- | ---- |
| Phe | Lys | Pro | Asp | Tyr | Pro | Glu | Met | Gln | Arg | Leu | Lys | Ala | Gln | Ile | Glu |      |
| 550 |     |     |     |     | 555 |     |     |     |     | 560 |     |     |     |     | 565 |      |

| gag | tcg | cgt | cgt | cag | atc | aat | ggc | gaa | gtc | atc | aat | atc | cgt | cag | tcg | 3761 |
| --- | --- | --- | --- | --- | --- | --- | --- | --- | --- | --- | --- | --- | --- | --- | --- | ---- |
| Glu | Ser | Arg | Arg | Gln | Ile | Asn | Gly | Glu | Val | Ile | Asn | Ile | Arg | Gln | Ser |      |
|     |     |     |     | 570 |     |     |     |     | 575 |     |     |     |     | 580 |     |      |

| ctg | aag | gcg | acc | tac | gac | gcc | tcc | gtg | cat | cag | gag | cag | ctg | ctc | aac | 3809 |
| --- | --- | --- | --- | --- | --- | --- | --- | --- | --- | --- | --- | --- | --- | --- | --- | ---- |
| Leu | Lys | Ala | Thr | Tyr | Asp | Ala | Ser | Val | His | Gln | Glu | Gln | Leu | Leu | Asn |      |
|     |     |     |     | 585 |     |     |     |     | 590 |     |     |     |     | 595 |     |      |

```
gac cgc atc gcc ggt ctg cgg tcc aac gag ctg gat ctg cag agc cgc          3857
Asp Arg Ile Ala Gly Leu Arg Ser Asn Glu Leu Asp Leu Gln Ser Arg
            600                 605                 610 agc atc cgc tac aac atg ctc aag cgc gac gtc gac acc aac cgc cag          3905
Ser Ile Arg Tyr Asn Met Leu Lys Arg Asp Val Asp Thr Asn Arg Gln
    615                 620                 625 ctc tac gat gcg ctc ctg cag cgc tac aag gaa atc ggc gtg gcg agc          3953
Leu Tyr Asp Ala Leu Leu Gln Arg Tyr Lys Glu Ile Gly Val Ala Ser
630                 635                 640                 645 aac gtg ggc gcc aac aac gtg acc atc gtc gat acc gca gac gtg cct          4001
Asn Val Gly Ala Asn Asn Val Thr Ile Val Asp Thr Ala Asp Val Pro
                650                 655                 660 acg tct aag act tcg ccg aaa ctc aaa ttg aac ctc gcg ttg ggc ctg          4049
Thr Ser Lys Thr Ser Pro Lys Leu Lys Leu Asn Leu Ala Leu Gly Leu
            665                 670                 675 atc ttt ggc gta ttc ctg ggc gtg gct gtg gct ctg gtt cgc tac ttc          4097
Ile Phe Gly Val Phe Leu Gly Val Ala Val Ala Leu Val Arg Tyr Phe
        680                 685                 690 ctg cgt ggg cct tct ccg agg tcg cgg ttg aac tga catcgtgatg              4143
Leu Arg Gly Pro Ser Pro Arg Ser Arg Leu Asn  *
    695                 700 ttgcaaaacg atggttaatt gaagtgacaa ctgattcagc gtggaaaagg tgggatcccg        4203
taaggtgcgg gctccctcgt ttgaaggttt gtctctgttg aaacaaaggg ctgtcgtgcg        4263
atctggggtc ggtaggtatt accgcggtga tcggacgaca ggatgattga aagctcgcgt        4323
gcgattcgta tgttcccccg catgcctgca ggtcgactct agagcggccg ccaccgcggt        4383
ggagctccaa ttcgccctat agtgagtcgt attacgcgcg ctcactggcc gtcgttttac       4443
aacgtcgtga ctgggaaaac cctggcgtta cccaacttaa tcgccttgca gcacatcccc       4503
ctttcgccag ctggcgtaat agcgaagagg cccgcaccga tcgcccttcc caacagttgc       4563
gcagcctgaa tggcgaatgg aaattgtaag cgttaatatt tgttaaaat cgcgttaaa        4623 ttttgttaa atcagctcat tttttaacca ataggccgac tgcgatgagt ggcagggcgg        4683
ggcgtaattt ttttaaggca gttattggtg cccttaaacg cctggtgcta cgcctgaata       4743
agtgataata agcggatgaa tggcagaaat tcgaaagcaa attcgacccg gtcgtcggtt       4803
cagggcaggg tcgttaaata gccgcttatg tctattgctg gtttaccggt ttattgacta       4863
ccggaagcag tgtgaccgtg tgcttctcaa atgcctgagg ccagtttgct caggctctcc       4923
ccgtggaggt aataattgac gatatgatca tttattctgc ctcccagagc ctgataaaaa       4983
cggtgaatcc gttagcgagg tgccgccggc ttccattcag gtcgaggtgg cccggctcca       5043
tgcaccgcga cgcaacgcgg ggaggcagac aaggtatagg gcggcgaggc ggctacagcc       5103
gatagtctgg aacagcgcac ttacgggttg ctgcgcaacc caagtgctac cggcgcggca       5163
gcgtgacccg tgtcggcggc tccaacggct cgccatcgtc cagaaaacac ggctcatcgg       5223
gcatcggcag gcgctgctgc ccgcgccgtt cccattcctc cgtttcggtc aaggctggca       5283
ggtctggttc catgcccgga atgccgggct ggctgggcgg ctcctcgccg ggccggtcg        5343 gtagttgctg ctcgcccgga tacagggtcg ggatgcggcg caggtcgcca tgccccaaca       5403
gcgattcgtc ctggtcgtcg tgatcaacca ccacggcggc actgaacacc gacaggcgca       5463
actggtcgcg gggctggccc cacgccacgc ggtcattgac cacgtaggcc gacacggtgc       5523
cggggccgtt gagcttcacg acggagatcc agcgctcggc caccaagtcc ttgactgcgt       5583
attggaccgt ccgcaaagaa cgtccgatga gcttggaaag tgtcttctgg ctgaccacca       5643
```

-continued

```
cggcgttctg gtggcccatc tgcgccacga ggtgatgcag cagcattgcc gccgtgggtt   5703
tcctcgcaat aagcccggcc cacgcctcat gcgctttgcg ttccgtttgc acccagtgac   5763
cgggcttgtt cttggcttga atgccgattt ctctggactg cgtggccatg cttatctcca   5823
tgcggtaggg tgccgcacgg ttgcggcacc atgcgcaatc agctgcaact tttcggcagc   5883
gcgacaacaa ttatgcgttg cgtaaaagtg gcagtcaatt acagattttc tttaacctac   5943
gcaatgagct attgcggggg gtgccgcaat gagctgttgc gtacccccct tttttaagtt   6003
gttgattttt aagtctttcg catttcgccc tatatctagt tctttggtgc ccaaagaagg   6063
gcacccctgc ggggttcccc cacgccttcg gcgcggctcc ccctccggca aaaagtggcc   6123
cctccggggc ttgttgatcg actgcgcggc cttcggcctt gcccaaggtg gcgctgcccc   6183
cttggaaccc ccgcactcgc cgccgtgagg ctcgggggc aggcgggcgg gcttcgcctt   6243
cgactgcccc cactcgcata ggcttgggtc gttccaggcg cgtcaaggcc aagccgctgc   6303
gcggtcgctg cgcgagcctt gacccgcctt ccacttggtg tccaaccggc aagcgaagcg   6363
cgcaggccgc aggccggagg cttttcccca gagaaaatta aaaaaattga tggggcaagg   6423
ccgcaggccg cgcagttgga gccggtgggt atgtggtcga aggctgggta gccggtgggc   6483
aatccctgtg gtcaagctcg tgggcaggcg cagcctgtcc atcagcttgt ccagcagggt   6543
tgtccacggg ccgagcgaag cgagccagcc ggtggccgct cgcggccatc gtccacatat   6603
ccacgggctg gcaagggagc gcagcgaccg cgcagggcga agcccggaga gcaagcccgt   6663
agggcgccgc agccgccgta ggcggtcacg actttgcgaa gcaaagtcta gtgagtatac   6723
tcaagcattg agtggcccgc cggaggcacc gccttgcgct gccccgtcg agccggttgg   6783 acaccaaaag ggaggggcag gcatggcggc atacgcgatc atgcgatgca agaagctggc   6843
gaaaatgggc aacgtggcgg ccagtctcaa gcacgcctac cgcgagcgcg agacgcccaa   6903
cgctgacgcc agcaggacgc cagagaacga gcactgggcg gccagcagca ccgatgaagc   6963
gatgggccga ctgcgcgagt tgctgccaga gaagcggcgc aaggacgctg tgttggcggt   7023
cgagtacgtc atgacggcca gcccggaatg gtggaagtcg gccagccaag aacagcaggc   7083
ggcgttcttc gagaaggcgc acaagtggct ggcggacaag tacggggcgg atcgcatcgt   7143
gacggccagc atccaccgtg acgaaaccag cccgcacatg accgcgttcg tggtgccgct   7203
gacgcaggac ggcaggctgt cggccaagga gttcatcggc aacaaagcgc agatgacccg   7263
cgaccagacc acgtttgcgg ccgctgtggc cgatctaggg ctgcaacggg gcatcgaggg   7323
cagcaaggca cgtcacacgc gcattcaggc gttctacgag gccctggagc ggccaccagt   7383
gggccacgtc accatcagcc cgcaagcggt cgagccacgc gcctatgcac cgcagggatt   7443
ggccgaaaag ctgggaatct caaagcgcgt tgagacgccg gaagccgtgg ccgaccggct   7503
gacaaaagcg gttcggcagg ggtatgagcc tgccctacag gccgccgcag gagcgcgtga   7563
gatgcgcaag aaggccgatc aagcccaaga gacggcccga g                       7604
```

<210> SEQ ID NO 2
<211> LENGTH: 232
<212> TYPE: PRT
<213> ORGANISM: Xanthomomas campestris

<400> SEQUENCE: 2

```
Met Lys Lys Leu Ile Gly Arg Leu Cys Gln Gly Leu Ser Leu Ala Leu
 1               5                  10                  15

Leu Cys Ser Met Ser Leu Gly Ala Cys Ser Thr Gly Pro Glu Met Ala
            20                  25                  30
```

```
Ser Ser Leu Pro His Pro Asp Pro Leu Ala Met Ser Thr Val Gln Pro
            35                  40                  45

Glu Tyr Arg Leu Ala Pro Gly Asp Leu Leu Val Lys Val Phe Gln
 50                  55                  60

Ile Asp Asp Leu Glu Arg Gln Val Arg Ile Asp Gln Asn Gly His Ile
 65                  70                  75                  80

Ser Leu Pro Leu Ile Gly Asp Val Lys Ala Gly Leu Gly Val Gly
                85                  90                  95

Glu Leu Glu Lys Leu Val Ala Asp Arg Tyr Arg Ala Gly Tyr Leu Gln
                100                 105                 110

Gln Pro Gln Ile Ser Val Phe Val Gln Glu Ser Asn Gly Arg Arg Val
                115                 120                 125

Thr Val Thr Gly Ala Val Asp Glu Pro Gly Ile Tyr Pro Val Ile Gly
            130                 135                 140

Ala Asn Leu Thr Leu Gln Gln Ala Ile Ala Gln Ala Lys Gly Val Ser
145                 150                 155                 160

Thr Val Ala Ser Arg Gly Asn Val Ile Val Phe Arg Met Val Asn Gly
                165                 170                 175

Gln Lys Met Ile Ala Arg Phe Asp Leu Thr Glu Ile Glu Lys Gly Ala
                180                 185                 190

Asn Pro Asp Pro Glu Ile Tyr Gly Gly Asp Ile Val Val Tyr Arg
                195                 200                 205

Ser Asp Ala Arg Val Trp Leu Arg Thr Met Leu Glu Leu Thr Pro Leu
210                 215                 220

Val Met Val Trp Arg Ala Tyr Arg
225                 230

<210> SEQ ID NO 3
<211> LENGTH: 472
<212> TYPE: PRT
<213> ORGANISM: Xanthomomas campestris

<400> SEQUENCE: 3

Met Asn Ser Asp Asn Arg Ser Ser Ser Gln Arg His Gly His Leu
 1               5                   10                  15

Glu Leu Ala Asp Val Asp Leu Met Asp Tyr Trp Arg Ala Leu Val Ser
                20                  25                  30

Gln Leu Trp Leu Ile Ile Leu Ile Ala Val Gly Ala Leu Leu Leu Ala
            35                  40                  45

Phe Gly Ile Thr Met Leu Met Pro Glu Lys Tyr Arg Ala Thr Ser Thr
 50                  55                  60

Leu Gln Ile Glu Arg Asp Ser Leu Asn Val Val Asn Val Asp Asn Leu
 65                  70                  75                  80

Met Pro Val Glu Ser Pro Gln Asp Arg Asp Phe Tyr Gln Thr Gln Tyr
                85                  90                  95

Gln Leu Leu Gln Ser Arg Ser Leu Ala Arg Ala Val Ile Arg Glu Ala
                100                 105                 110

Lys Leu Asp Gln Glu Pro Ala Phe Lys Glu Gln Val Glu Glu Ala Leu
            115                 120                 125

Ala Lys Ala Ala Glu Lys Asn Pro Glu Ala Gly Lys Ser Leu Asp Ser
130                 135                 140

Arg Gln Ala Ile Val Glu Arg Ser Leu Thr Asp Thr Leu Leu Ala Gly
145                 150                 155                 160

Leu Val Val Glu Pro Ile Leu Asn Ser Arg Leu Val Tyr Val Asn Tyr
```

-continued

```
                165                 170                 175

Asp Ser Pro Asp Pro Val Leu Ala Ala Lys Ile Ala Asn Thr Tyr Pro
            180                 185                 190
Lys Val Phe Ile Val Ser Thr Gln Glu Arg Arg Met Lys Ala Ser Ser
        195                 200                 205
Phe Ala Thr Gln Phe Leu Ala Glu Arg Leu Lys Gln Leu Arg Glu Lys
    210                 215                 220
Val Glu Asp Ser Glu Lys Asp Leu Val Ser Tyr Ser Thr Glu Glu Gln
225                 230                 235                 240
Ile Val Ser Val Gly Asp Asp Lys Pro Ser Leu Pro Ala Gln Asn Leu
                245                 250                 255
Thr Asp Leu Asn Ala Leu Leu Ala Ser Ala Gln Asp Ala Arg Ile Lys
            260                 265                 270
Ala Glu Ser Ala Trp Arg Gln Ala Ser Ser Gly Asp Gly Met Ser Leu
        275                 280                 285
Pro Gln Val Leu Ser Ser Pro Leu Ile Gln Ser Leu Arg Ser Glu Gln
    290                 295                 300
Val Arg Leu Thr Ser Glu Tyr Gln Gln Lys Leu Ser Thr Phe Lys Pro
305                 310                 315                 320

Asp Tyr Pro Glu Met Gln Arg Leu Lys Ala Gln Ile Glu Glu Ser Arg
                325                 330                 335
Arg Gln Ile Asn Gly Glu Val Ile Asn Ile Arg Gln Ser Leu Lys Ala
            340                 345                 350
Thr Tyr Asp Ala Ser Val His Gln Glu Gln Leu Leu Asn Asp Arg Ile
        355                 360                 365
Ala Gly Leu Arg Ser Asn Glu Leu Asp Leu Gln Ser Arg Ser Ile Arg
    370                 375                 380
Tyr Asn Met Leu Lys Arg Asp Val Asp Thr Asn Arg Gln Leu Tyr Asp
385                 390                 395                 400
Ala Leu Leu Gln Arg Tyr Lys Glu Ile Gly Val Ala Ser Asn Val Gly
                405                 410                 415
Ala Asn Asn Val Thr Ile Val Asp Thr Ala Asp Val Pro Thr Ser Lys
            420                 425                 430
Thr Ser Pro Lys Leu Lys Leu Asn Leu Ala Leu Gly Leu Ile Phe Gly
        435                 440                 445
Val Phe Leu Gly Val Ala Val Ala Leu Val Arg Tyr Phe Leu Arg Gly
    450                 455                 460
Pro Ser Pro Arg Ser Arg Leu Asn
465                 470

<210> SEQ ID NO 4
<211> LENGTH: 31
<212> TYPE: DNA
<213> ORGANISM: Xanthomomas campestris

<400> SEQUENCE: 4
ggaattccat atgttgatgc ccgagaagta c                                      31

<210> SEQ ID NO 5
<211> LENGTH: 33
<212> TYPE: DNA
<213> ORGANISM: Xanthomomas campestris

<400> SEQUENCE: 5
cgggatcctc aaaagatcag gcccaacgcg agg                                    33
```

HIGH VISCOSITY XANTHAN POLYMER PREPARATIONS

This is a divisional of U.S. application. Ser. No. 10/802,034, filed Mar. 17, 2004, now U.S. Pat. No. 7,439,044. Priority benefit of U.S. Provisional Application No. 60/456,245, filed Mar. 21, 2003, is claimed. The prior applications are incorporated herein by reference in their entirety.

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

FIELD OF THE INVENTION

The invention relates to the field of microbial products. In particular it relates to microbial products having improved properties for various industrial purposes.

BACKGROUND OF THE INVENTION

The chemical structure of xanthan is composed of a linear cellulosic (1→4)-β-D-glucose polymer with trisaccharide side chains composed of mannose, glucuronic acid and mannose, attached to alternate glucose residue in the backbone. (Milas and Rinaudo, Carbohydrate Research, 76, 189-196, 1979). Thus xanthan can be described as a branched chain polymer with a pentasaccharide repeat unit; normal xanthan typically has 2000-3000 pentasaccharide repeat units. The xanthan polymer is typically modified by acetylation and pyruvylation of the mannose residues.

The fermentation of carbohydrates to produce the biosynthetic water-soluble polysaccharide xanthan gumBy the action of *Xanthomonas* bacteria is well known. The earliest work was conducted by the United States Department of Agriculture and is described in U.S. Pat. No. 3,000,790. *Xanthomonas* hydrophilic colloid ("xanthan") is an exocellular heteropolysaccharide.

Xanthan is produced by aerobic submerged fermentation of a bacterium of the genus *Xanthomonas*. The fermentation medium typically contains carbohydrate (such as sugar), trace elements and other nutrients. Once fermentation is complete, the resulting fermentation broth (solution) is typically heat-treated. It is well established that heat treatment of xanthan fermentation broths and solutions leads to a conformational change of native xanthan at or above a transition temperature ($T_M$) to produce a higher viscosity xanthan. Heat treatment also has the beneficial effect of destroying viable microorganisms and undesired enzyme activities in the xanthan. Following heat-treatment, the xanthan is recovered by alcohol precipitation. However, heat treatment of xanthan fermentation broths also has disadvantages, such as thermal degradation of the xanthan. Heating xanthan solutions or broths beyond $T_M$ or holding them at temperatures above $T_M$ for more than a few seconds leads to thermal degradation of the xanthan. Degradation of xanthan irreversibly reduces its viscosity. Accordingly, heat treatment is an important technique with which to control the quality and consistency of xanthan.

Xanthan quality is primarily determined by two viscosity tests: the Low Shear Rate Viscosity ("LSRV") in tap water solutions and the Sea Water Viscosity ("SWV") in high salt solutions. Pasteurization of xanthan fermentation broths at temperatures at or above $T_M$ has been found to yield xanthan of a higher viscosity as indicated by higher LSRV and SWV values.

Xanthan polymer is used in many contexts. Xanthan has a wide variety of industrial applications including use in oil well drilling muds, as a viscosity control additive in secondary recovery of petroleum by water flooding, as a thickener in foods, as a stabilizing agent, and as a emulsifying, suspending and sizing agent (Encyclopedia of Polymer Science and Engineering, 2nd Edition, Editors John Wiley & Sons, 901-918, 1989). Xanthan can also be used in cosmetic preparations, pharmaceutical vehicles and similar compositions.

There is a need in the art to produce a xanthan polymer with higher specific viscosity characteristics in the unpasteurized state. Such a higher specific viscosity xanthan polymer could provide more viscosity at equivalent xanthan concentrations, for example, for food, industrial, and oilfield applications.

BRIEF SUMMARY OF THE INVENTION

In a first embodiment an unpasteurized xanthan composition is provided. The composition can be provided by a cell which over-expresses gumB and gumC. It has an intrinsic viscosity which is at least 20% greater than xanthan from a corresponding strain which does not over-express gumB and gumC.

In a second embodiment a xanthan composition is provided. It comprises a population of xanthan molecules having a range of molecular lengths. At least 1% of the population has a length greater than 3 um as measured by atomic force microscopy.

In a third embodiment of the invention a method is provided for producing a xanthan polymer preparation having increased viscosity relative to that produced by a wild-type strain. The amount of gene product of gumB and gumC is selectively increased in a *Xanthomonas campestris* culture. The amount of a gene product of orfX is not selectively increased. Nor is the amount of a product of a gene selected from the group consisting of gumD-gumG selectively increased. A higher viscosity xanthan polymer preparation is thereby produced by the culture.

In a fourth embodiment of the invention a method is provided for producing a xanthan polymer preparation having increased viscosity relative to that produced by a wild-type strain. A *Xanthomonas campestris* strain is cultured in a culture medium under conditions in which it produces a xanthan polymer. The strain selectively produces relative to a wild-type strain more gene product of gumB and gumC but not of orfX nor of a gene selected from the group consisting of gumD-gumG.

In a fifth embodiment of the invention an unpasteurized xanthan composition is provided. The composition is made by a cell which over-expresses gumB and gumC. The composition has a seawater viscosity which is at least 10% greater than xanthan from a corresponding strain which does not over-express gumB and gumC.

The present invention thus provides the art with xanthan compositions which have increased viscosity relative to those similarly produced by corresponding wild-type strains.

BRIEF DESCRIPTION OF THE DRAWINGS

FIG. 1 shows genetic constructs relative to a genetic map of the gumB-M operon, also known as the xpsB-M (xanthan polysaccharide synthesis) operon.

FIGS. 2A and 2B show Western blot analyses of gumB and gumC protein product expression, respectively.

FIG. 3 shows an intrinsic viscosity plot for xanthan gum samples, one of which over-expresses gumB and gumC gene products due to the presence of a plasmid carrying extra copies of the genes.

DETAILED DESCRIPTION OF THE INVENTION

It is a discovery of the present inventors that overexpression of gumB and gumC gene products relative to other genes in their operon, yields xanthan products with higher viscosity on a per weight basis. While applicants do not wish to be bound by any particular theory of operation, it appears that a shift in the ratio of certain gene products leads to a shift in the size distribution of xanthan polymer molecules. A significant number of molecules are of higher molecular length than when xanthan is made by a wild-type cell. These longer molecules lead to a higher viscosity of the population or preparation.

It is known in the art that increases in viscosity can be obtained by pasteurizing xanthan preparations. See Talashek et al., U.S. Pat. No. 6,391,596. However, the increased viscosity found as the result of overexpression of gumB and gumC is observed even in the absence of pasteurization. Nonetheless subsequent pasteurization of the products of the present invention will yield an even more viscous preparation.

Overexpression of both gumB and gumC appear to be required to achieve the increased viscosity. When either gene was tested alone, the increase was not observed. The overexpression of gumB and gumC can be assessed relative to other genes of the gumB-M operon. While overexpression relative to any of those genes may be sufficient to achieve the effect, overexpression with respect to orfX and gumD may be particularly significant. OrfX is a small open reading frame that was previously published as a segment of the genome designated as gumA, immediately upstream of gumB. Recently two open reading frames have been discerned in the former gumA region, ihf and orfX. Overexpression relative to all of the genes gumD-gumM may be desirable.

Overexpression of the desired gene products may be achieved by any means known in the art, including, but not limited to, introducing additional copies of the genes encoding the desired gene products to a *Xanthomonas campestris* cell or other bacterium that makes xanthan, and induction of the desired gene products using for example an inducible promoter. Other bacteria that make xanthan include those that have been genetically engineered to contain the xanthan biosynthetic genes. The gumB and gumC genes can be introduced on one or more vectors, i.e., in combination or individually.

Inducible promoters which can be used according to the invention include any that are known in the art, including the lac promoter, the ara promoter, the tet promoter, and the tac promoter. Natural and artificial inducing agents for these promoters are known in the art, and any can be used as is convenient. Additional copies of genes can be introduced on plasmids or viral vectors, for example. Additional copies of the desired genes can be maintained extrachromosomally or can be integrated into the genome.

Recovery of xanthan from a culture broth typically involves one or more processing steps. The xanthan may be heat-treated. The xanthan may be precipitated with an alcohol, such as isopropyl alcohol, ethyl alcohol, or propyl alcohol. Typically the cells are not specifically removed from the culture broth.

Xanthan molecules produced biosynthetically typically have a distribution of sizes. The increased viscosity of the present invention may be achieved by increasing the number of molecules having a much longer than average length, or by increasing to a greater degree the number of molecules having a somewhat longer than average length. The number of molecules which have increased length need not be huge. At least 1, 3, 5, 7, 9, or 11% of the molecules with an increased length may be sufficient. The molecules of increased length may be greater than 3, 4, 5, 6, 7, 8, or 9 um, as measured by atomic force microscopy. The percentage of the mass of the total xanthan population contributed by the molecules which are longer than 3, 4, 5, 6, 7, 8, or 9 um will be greater than their number proportion in the population. Thus at least 1, 3, 5, 10, 15, 20, or 25% of the total mass of the xanthan molecules may be contributed by molecules having a greater than 3 um length.

Intrinsic viscosity measurements are yet another way to characterize the preparations of the present invention. Increases seen using this type of measurement may be as great as 5, 10, 15, 20, 25, 30, or 35% over that produced by wild-type strains. Proper controls for comparison purposes are those corresponding strains which are most closely related to the strains being tested. Thus if testing strains that have additional copies of gumB and gumC, the best control will have the same genetic complement but for the presence of the additional copies of gumB and gumC. If testing cultures that have been induced by an inducer to produce more gumB and gumC gene product, then the best control will be cultures of the same strain that have not been induced. Sea water viscosity can also be used to characterize preparations of the present invention. Increases seen using this type of measurement may be as great as 5, 10, 15, 20, 25, 30, or 35% over that produced by wild-type strains.

Xanthan is used as a component in a number of products to improve properties. The properties may include viscosity, suspension of particulates, mouth feel, bulk, to name just a few. Other properties include water-binding, thickener, emulsion stabilizing, foam enhancing, and sheer-thinning. Such products include foods, such as salad dressings, syrups, juice drinks, and frozen desserts. Such products also include printing dyes, oil drilling fluids, ceramic glazes, and pharmaceutical compositions. In the latter case, xanthan can be used as a carrier or as a controlled release matrix. Other products where xanthan can be used include cleaning liquids, paint and ink, wallpaper adhesives, pesticides, toothpastes, and enzyme and cell immobilizers.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

EXAMPLES

Example 1

Strain Construction

To isolate a fragment carrying the complete gum gene region of *X. campestris*, a genomic library of the wild type *X. campestris* strain, NRRL B-1459 (1), was constructed with the broad-host-range cosmid vector pRK311 (2) by cloning of total DNA partially digested with Sau3AI. This library was mated en masse from *E. coli* S17-1 (3) to the Gum$^-$ *X. campestris* mutant 2895 (4). One of the cosmids isolated from several mucoid exconjugants termed pIZD15-261 (5) contains a 16-kb fragment encompassing the complete gum region. See FIG. 1 for a graphic representation and Table 1 for a listing of the genes of the operon.

TABLE 1

List of genes designations in the chromosomal region encoding xanthan polysaccharide synthesis

| X. campestris ATCC13951 (NRRL B-1459) | X. campestris pv. campestris ATCC33913 | Chromosomal Location* | Function |
|---|---|---|---|
| inf | himA (XCC2457) | 2918744-2918448 | integration host factor, alpha chain |
| orfX | (XCC2456) | 2918464-2918111 | transcriptional regulator |
| xpsB | gumB (XCC2454) | 2917444-2916806 | xanthan export |
| xpsC | gumC (XCC2453) | 2916731-2915385 | xanthan export |
| xpsD | gumD (XCC2452) | 2915139-2913688 | glucasyl transferase |
| xpsE | gumE (XCC2451) | 2913602-2912307 | xanthan polymerization |
| xpsF | gumF (XCC2450) | 2912307-2911216 | acetyl transferase |
| xpsG | gumG (XCC2449) | 2911216-2910149 | acetyl transferase |
| xpsH | gumH (XCC2448) | 2910078-2908939 | mannosyl transferase |
| xpsI | gumI (XCC2447) | 2908939-2907893 | mannosyl transferase |
| xpsJ | gumJ (XCC2446) | 2907893-2906397 | xanthan export |
| xpsK | gumK (XCC2445) | 2906014-2905130 | glucuronic transferase |
| xpsL | gumL (XCC2444) | 2905086-2904295 | pyruvyl transferase |
| xpsM | gumM (XCC2443) | 2904284-2903496 | glucosyl transferase |
| orf165 | (XCC2442) | 2903458-2902964 | unknown conserved hypothetical |

*Gene locations are according to the genome sequence of X. campestris pv. campestris ATCC33913 (GenBank deposition: AE008922) as described by da Silva, A. C. R., et al., (Nature, Vol. 417, pg. 459-463, 2002)

For the construction of the pBBR5-BC plasmid, a 4026 bp fragment from pIZD15-261 digested with SpeI-BglII was cloned between the XbaI and BamBI sites of pKmob19 (8), giving rise to pGum02-19S (5). A 2855 bp fragment was released from plasmid pGum02-19S by digestion with SphI. This fragment was cloned into pUC18 (9), which was previously digested with SphI, forming pUC18-BCAS.

The final plasmid (pBBR5-BC) was constructed by cloning the HindIII-XbaI fragment, containing the gum promoter and gumB and gumC genes, into HindIII-XbaI digested pBBR1-MCS5 (10) (GenBank accession no. U25061).

The nucleotide sequence of the resulting pBBR5-BC plasmid is shown in SEQ ID NO: 1. (The predicted amino acid sequences of gumB and gumC are shown in SEQ ID NOs: 2 and 3, respectively. This broad-host-range, medium-copy-number plasmid is 7.6 kb in length and is compatible with IncP, IncQ and IncW group plasmids, as well as with ColE1- and P15a-based replicons. The presence of an origin of transfer (mobRK2) enables its transference by conjugation into a wide range of bacteria when the RK2 transfer functions are provided in trans. It also carries the gentamicin resistance gene and it contains, the pBluescript II KS multiple cloning site located within the gene encoding the LacZ α peptide (pBluescript II KS from Stratagene, La Jolla, Calif., USA).

To verify the expression of GumB and GumC proteins from pBBR5-BC, the plasmid was introduced into X. campestris mutant 1231, in which the entire gum (xps) gene cluster was deleted. Both proteins were detected by Western blot in the mutant strain.

TABLE 2

Bacterial strains and plasmids used or constructed in this work.

| Bacterial strain or plasmid | Relevant characteristics | Source (reference) |
|---|---|---|
| E. coli. | | |
| DH5α | F-endA1 hsdR17 supE44 thi-1 recA1 gyrA relA1 ΔlacU169 (φ80dlacZΔM15) | New England Biolabs |
| S17-1 | E. coli 294 RP4-2-Tc::Mu-Km::Tn7 | (3) |
| JM109 | F' traD36 proA$^+$B$^+$ lacI$^q$ Δ(lacZ)M15/Δ(lac-proAB) glnV44 eI4$^-$ gyrA96 ompT hsdS$_B$(r$_B^-$ m$_B^-$) gal [dcm] [lon] | New England Biolabs |
| BL21(DE3) | F-ompT hsdS$_B$(r$_B^-$ m$_B^-$) gal [dcm] [lon] (DE3) | Novagen |
| X. campestris | | |
| NRRL B-1459 | Wild type. | (1) |
| 2895 | Rif$^r$ xpsI-26I | (11) |
| 1231 | Tc::Tn 10 ΔxpsI | C.P. Kelco |
| XWCM1 | Mutant of NRRL B-1459 | C.P. Kelco |
| PRM-1 | Mutant of NRRL B-1459 | C.P. Kelco |

TABLE 2-continued

Bacterial strains and plasmids used or constructed in this work.

| Bacterial strain or plasmid | Relevant characteristics | Source (reference) |
|---|---|---|
| Plasmids | | |
| pRK311 | oriV(RK2) Tc$^r$ oriT(mob$^+$) tra$^-$ λcos lacZ(α) | (2) |
| pIZD15-261 | Cosmid based on pRK311 carrying the X. campestris gum region. | (5) |
| pK19mob | Km$^r$, pK19 derivative, mob-site | (8) |
| pgum02-19AS | pK19mob vector carrying the gum fragment 770-4795$^a$ | (5) |
| pUC18 | Ap$^r$, ColE1, lacZα$^+$ | (9) |
| pUC18-BCAS | pUC18 vector carrying the gum fragment 770-3610$^a$ | This work |
| pBBR1-MCS5 | Gm$^r$, pBBR1CM derivative, mob-site, lacZα$^+$ | (10) |
| pBBR5-BC | PBBR1-MCS5 carrying the gum fragment 770-3610$^a$ | This work |
| pQE-Xps#6 | pQE30 vector carrying the gum fragment 1336-1971$^a$ | C.P. Kelco |
| pQE30 | Ap$^r$ | Qiagen |
| pREP4 | Km$^r$ | Qiagen |
| pET-C | pET22b(+) vector carrying the gum fragment 2135-3319$^a$ | This work |
| pET22b+ | Ap$^r$ | Novagen |
| pH336 | pRK290 carrying gum BamHI fragments1-15052$^a$ | Synergen |
| pCOS6 | pRK293 carrying SalI fragments 1-14585a sad upstream xps I DNA | CP Kelco |
| pFD5 | pRK404 carrying partial BamHI gum fragment 318-3464$^a$ | Ielpi |
| pCHC22 | pRK293 carrying SalI fragments 1-9223a and upstream xps I DNA | (4) |
| pBBR-prom | pBBR1-MCS5 carrying gum fragment 1000-1276$^a$ | This work |
| pBBR5-B | pBBR1-MCS5 carrying gum fragment 770-1979$^a$ | This work |
| pBBR-promC | pBBR1-MCS5 carrying gum fragment 1979-3459$^a$ | This work |

$^a$Numbers correspond to the position in the nucleotide sequence of the gum region (GenBank, accession number U22511)

Bacterial strains, plasmids, and growth conditions. The strains and plasmids used in this study are listed in Table 2. *E. coli* strains were grown in Luria-Bertani medium at 37° C. *X. campestris* strains were grown in TY (5 g of tryptone, 3 g of yeast extract, and 0.7 g of CaCl$_2$ per liter of H$_2$O) or in YM medium (12) at 28° C. Antibiotics from Sigma (St. Louis, Mo.) were supplemented as required at the following concentrations (in micrograms per milliliter): for *X. campestris*, gentamicin, 30; and tetracycline, 10; for *E. coli*, gentamicin, 10; kanamycin, 30; ampicillin, 100; and tetracycline, 10.

DNA biochemistry. Plasmid DNA from *E. coli* and *X. campestris* was prepared by using the QIAprep Spin Miniprep Kit (QIAGEN, Hilden, Germany). DNA restriction, agarose gel electrophoresis and cloning procedures were carried out in accordance with established protocols (13). All constructs were verified by DNA sequencing. Plasmid DNA was introduced into *E. coli* and *X. campestris* cells by electroporation as instructed by Bio-Rad (Richmond, Calif.) (used parameters: *E. coli*: 200Ω, 25 μF, 2500V and *X. campestris*: 1000Ω, 25 μF, 2500V).

Analysis of nucleotide and protein sequences. The nucleotide and amino acid sequences were analyzed by using the MacVector Sequence Analysis Software (Oxford Molecular Limited, Cambridge, UK).

Example 2

Western Analysis of gumB and gumC Expression

Western Analysis confirmed that gumB and gumC gene products are being over-expressed in the *X. campestris* strain with extra copies of gumB and gumC. See FIG. 2.

Example 3

Intrinsic Viscosity Determination

Xanthan samples prepared from *X. campestris* strains with (XWCM1/pBBR5BC) and without (XWCM1) multiple, plasmid encoded copies of the gumB and gumC genes were compared. Shake flask fermentations, using glucose as a carbon source, were carried out to obtain xanthan from these strains.

Intrinsic viscosity was determined by measuring viscosity on both purified and unpurified xanthan samples. An increase in the intrinsic viscosity for xanthan from *X. campestris* strain with multiple copies of gumB and gumC was observed. Intrinsic viscosity is proportional to the molecular weight for a given polymer type when measured under identical solvent and temperature conditions. Therefore, xanthan from *X. campestris* strain with multiple copies of gumB and gumC is of higher molecular weight compare to xanthan from control strain.

Methods: Five shake flasks each of the two broths were tested. The broths of each type were combined and the total volume measured. The broth was then precipitated in isopropyl alcohol. (Note: It was estimated that the broth contained approximately 3% gum. Measuring the total broth volume and multiplying by 3% gave the approximate dry gum weight. This approximation was used to calculate the amount of water required to produce approximately a 0.5% gum solution). The wet fibers of the precipitate were then immediately rehydrated with mixing in 0.01M NaCl to produce approximately a 0.5% gum solution. The fibers were mixed for three hours with good shear using a 3-blade 2 inch diameter propeller stirrer, then allowed to stand overnight. The following procedure was used to prepare the samples for intrinsic viscosity measurements.

Filter the ~0.5% gum solution, prepared above, using a Gelman Science 293 mm pressure filtration unit. The solution is first filtered through a 20μ Magna nylon filter (N22SP29325). The filter is pressurized to ~60 psi, and the solution collected into clean beakers. (Note: the filters are changed when the flow rate is reduced to ~5 drips per minute.

Following the first filtration step, the samples are filtered two more times using the above filtration unit. First, through a Millipore 8.0μ filter (SCWP 293 25), then through a Gelman Versapor® 293 mm 1.2μ filter (66397). The filtered sample is recovered in clean beakers following each filtration step.

After filtration, ~600 ml of the gum solution is placed into Spectra/Por® dialysis tubing 28.6 mm diameter Spectrum # S732706 (MWCO 12,000 to 14,000). The tubing is cut into lengths of ~18-20 inches, and a knot tied in one end. The solution is added to the tubing, filling it to within ~2 inches from the end. Tie a second knot in the tubing such that as little air as possible is trapped in the tubing. Continue until all the gum solution is in dialysis tubing.

Rinse the outside of the tubing containing the gum solution for ~1 minute with de-ionized water, then place the tubing into a container of 0.01M NaCl. The salt solution should completely cover the dialysis tubing.

Allow the tubing to sit in the 0.01M NaCl solution for 4 days, changing the NaCl solution daily. After the 4 days, cut open one end of the tubing and carefully transfer the gum solution to a clean beaker.

Solids are run on the filtered dialyzed solution using the following procedure:

Using an analytical balance capable of weighing to ±0.0002 g, weigh and record the weight of a clean aluminum weighing dish VWR Cat #25433-008. (A)

Using a clean pipet add approximately 10 ml of the gum solution to the aluminum pan and record the exact weight of the combined pan and gum solution. (B)

Place the pan with the solution into a 105° C. drying oven and allow to stand for 24 hours.

Remove the pan from the oven after 24 hours, cool and reweigh. Record the weight of the pan and remaining dried gum. (C)

Subtract the weight of the aluminum pan (A) from the weight of the pan plus the gum solution (B). Subtract the weight of the aluminum pan (A) from the weight of the dried gum plus the pan (C). Divide the first value (B−A) into the second (C−A). Multiply this value by 100 to obtain the % solids.

Note: Solids were run in triplicate for each filtered dialyzed solution using the above procedure. The calculated % solids were than averaged for each sample and the averaged value was used.

Based on the solids determination for each solution, the samples are diluted to 0.25% total gum concentration using 0.01M NaCl.

Intrinsic viscosity measurements were made using the Vilastic Viscoelasticity Analyzer (Vilastic Scientific, Inc., Austin, Tex., fitted with the 0.0537 cm radius×6.137 cm length tube. The instrument was calibrated with water prior to making measurements and verified after the measurements were completed. Measurements were conducted using the instruments TIMET software protocol, set to a frequency of 2.0 Hz, a constant strain of 1.0, and an integration time of 10 seconds. The temperature was maintained at 23.5° C. The samples were prepared by dilution of the 0.25% gum solution. Each dilution was mixed for 20 minutes, and allowed to stand refrigerated overnight before being measured. Six measurements were made for each dilution and averaged. Table 3 below shows the dilutions and the resultant averaged viscosities for each prepared sample.

TABLE 3

| Concentrations | Dilutions 0.25% X.G. (ml) | 0.01M NaCl (ml) | Viscosity Measurements XWCM1 Control | XWCM1/ pBBR5-BC |
|---|---|---|---|---|
| Solute 0.01M NaCl | 0 | 100 | .921 | .921 |
| 0.0025% | 1 | 99 | 1.114 | 1.165 |
| 0.0050% | 2 | 98 | 1.326 | 1.486 |
| 0.0075% | 3 | 97 | 1.537 | 1.829 |
| 0.0100% | 4 | 96 | 1.762 | 2.181 |
| 0.0150% | 6 | 94 | 2.302 | 2.963 |
| 0.0200% | 8 | 92 | 2.920 | 3.901 |

Intrinsic viscosities were determined by plotting the reduced specific viscosity ($\eta_{sp}/c$) against the gum concentration $\eta_{sp}/c=((\eta_c-\eta_o)/\eta_o)$ where $\eta_c$=viscosity of the gum. The intercept yields the intrinsic viscosity. See FIG. 3.

The increase in intrinsic viscosity for the XWCM1/pBBR5-BC variant is believed due to an increase in molecular weight. Intrinsic viscosity is proportional to the molecular weight for a given polymer type when measured under identical solvent and temperature conditions as done in this experiment. The relationship between [η] and molecular weight is given by the Mark-Houwink equation $[\eta]=kM^a$, where k and a are constants for a specified polymer type in a specified solvent at a specified temperature. Because the constant "a" is positive number, an increase in [η] can only be obtained by an increase in the molecular weight (M) unless the samples have a different molecular conformation in which case the Mark-Houwink equation is not obeyed.

Example 4

Procedure—Low Shear Rate Viscosity Measurement

Low shear rate viscosity measurements were performed on purified xanthan samples. The procedure used to measure LSRV is detailed below. Increased viscosity for xanthan from a strain with multiple copies of gumB and gumC compared to xanthan from a control strain was observed. The data suggest that over-expression of both gumB and gumC is required for increased chain length; over-expression of either gumB or gumC individually is not sufficient to increase chain length.

Material and Equipment:
1. Standard (synthetic) Tap Water (water containing 1000 ppm NaCl and 40 ppm $Ca^{++}$ or 147 ppm $CaCl_2.2H_2O$): Prepare by dissolving in 20 Liters of distilled water contained in a suitable container, 20 gm of reagent grade NaCl and 2.94 gm of reagent grade $CaCl_2.2H_2O$.
2. Balance capable of accurately measuring to 0.01 gm.
3. Brookfield LV Viscometer, Spindle #1, and spindle Guard.
4. Standard laboratory glassware.
5. Standard laboratory stirring bench. An RAE stirring motor (C25U) and stirring shaft (5/16") with 3-bladed propeller may be substituted.

Procedure:
1. To 299 ml of synthetic tap water weighed in a 600 ml Berzelius (tall form)
   beaker, slowly add 0.75 gm (weighed to the nearest 0.01 gm) of product,
   while stirring at 800 rpm.

2. After stirring four hours at 800 rpm, remove the solution from the stirring
bench, and allow to stand for 30 minutes.
3. Adjust the temperature to room temperature and measure the viscosity using a Brookfield
LV Viscometer with the No. 1 spindle at 3 rpm. Record the viscosity after allowing the spindle to rotate for 3 minutes.

Example 5

Quantification of Protein Expression

Cell lysates were subjected to Western blot and immunodetection analysis to establish the level of plasmid encoded GumB and GumC. Four independent blots were analyzed. Although absolute values for the same sample were not reproducible in each quantification, the relative quantities between samples remained the same in all the measurements.

Preparation of antibodies raised against GumB and GumC. An 1184 bp DNA fragment encoding amino acid residues 53-447 of the GumC protein was produced by PCR amplification. The following primers were used: F2135: 5'GGAAT-TCCATATGTTGATGCCCGAGAAGTAC-3' (SEQ ID NO: 4) and B3319: 5'CGGGATCCTCAAAAGATCAGGC-CCAACGCGAGG-3 (SEQ ID NO: 5)'. The PCR product was digested with NdeI and BamHI subcloned into pET22b(+) and the resulting plasmid (pET-C) introduced into the *E. coli* strain BL21(DE3).

*E. coli* BL21(pET-C) grown in L-broth containing 50 μg carbenicillin ml$^{-1}$ to OD$_{600}$ 0.6 was induced with 1 mM IPTG for 3 h. Total cell lysates were prepared by treating with 1 mg lysozyme ml$^{-1}$ in lysis buffer (50 mM Tris/HCl pH8, 1 mM EDTA pH8, 100 mM NaCl, 1 mM PMSF, 0.1 mg DNase ml$^{-1}$, 0.5% Triton X-100) at 37° C. for 30 min, followed by sonication on ice. Cell debris was removed by low speed centrifugation (Eppendof, 4000×g, 5 min) and the supernatant was fractionated in a soluble and in a pellet (inclusion bodies) fraction by centrifugation at 14000×g for 10 min. Pellet fraction was washed twice with lysis buffer, in a volume identical to that of the original cell lysate, once with 2 mg DOC ml$^{-1}$ in lysis buffer followed by three washes with water. After treatment, proteins were separated by SDS-PAGE and the major band containing the overproduced GumC protein was cut and eluted for immunizing rabbits.

*E. coli* JM109(pQE-Xps#6, pREP4) grown in L-broth containing 50 μg carbenicillin, 25 μg kanamycin ml$^{-1}$ to OD$_{600}$ 0.6 was induced with 1 mM IPTG for 3 h. Total cell lysates were prepared by treating with 1 mg lysozyme ml$^{-1}$ in lysis buffer (50 mM Tris/HCl pH8, 1 mM EDTA pH8, 100 mM NaCl, 1 mM PMSF, 0.1 mg DNase ml$^{-1}$, 0.5% Triton X-100) at 37° C. for 30 min, followed by sonication on ice. Cell debris was removed by low speed centrifugation (Eppendof, 4000×g, 5 min) and the supernatant was fractionated in a soluble and in an pellet (inclusion bodies) fraction by centrifugation at 14000×g for 10 min. Pellet fraction was washed twice with lysis buffer, resuspended in 6 M guanidine hydrochloride in 100 mM Phosphate buffer (pH7), 5 mM DTT, 5 mM EDTA and inclusion bodies were chromatographed on an FPLC Superdex HR200 (Pharmacia Biotech) pre-equilibrated with buffer D (4 M GdnHCl, 50 mM Phosphate buffer (pH7), 150 mM NaCl). Fractions containing GumB were pooled and used to immunize mice.

Construction of plasmids pFD5, pBBR-promC, and pBBR5-B. A 3141 bp fragment containing gumB and gumC genes was obtained by partial digestion of pIZD15-261 with BamHI (#318 and #3459) and cloned into BamHI-digested pRK404 to yield plasmid pFD5. A 1480 bp fragment was isolated by digestion of pGum02-19 with EcoRI (#1979) and BamHI (#3459) and cloned in pBBR1MCS-5 previously digested with the same enzymes to yield pBBR-promC. Digestion of pGum02-19 with HindIII in the MCS and EcoRI (#1979) produced a 1233 bp fragment, which was cloned in pBBR1MCS-5 to yield plasmid pBBR5-B.

New Zealand white female rabbits were immunized using GumC prepared as described above. A primary injection of 500 μg of the protein with complete Freund's adjuvant was given to the rabbits, followed by three injections of 250 μg of the protein with incomplete adjuvant on alternate weeks. BALB/c female mice were immunized using GumB prepared as described above. A primary injection of 100 μg of the protein with complete Freund's adjuvant was given to the mice, followed by three injections of 50 μg of the protein with incomplete adjuvant once a week. Polyclonal antibodies were prepared as described by Harlow & Lane ((1999) *Using antibodies: a laboratory manual*, Cold Spring Harbor Laboratory Press, Cold Spring Harbor, N.Y.) and antisera were stored at −70° C. To obtain GumC-specific antibodies, the serum was adsorbed with both *E. coli* BL21(pET22b+) and Xc1231 acetone powders (Harlow & Lane, supra).

Protein extracts. Plasmids were introduced into the parental strain PRM-1 by electroporation. The resulting strains were grown in YM medium at 28° C. and 250 rpm to middle-logarithmic phase. Cells were harvested by centrifugation and the fresh-weight determined. The pellet was washed twice with 10 mM Tris/HCl, 10 mM EDTA (pH 8.0) to remove exopolysaccharide and resuspended in the same buffer at a concentration of 100 mg/ml. After addition of 100 μl Buffer A (10 mM Tris/HCl, 10 mM EDTA (pH 8.0), 1.5% SDS) to 50 μl of each sample, the mixture was incubated at room temperature for 10 min followed by incubation at 100° C. for 12 min. Cell lysate was centrifuged at 14000×g (Eppendorf 5415 C) for 5 min and the supernatant collected was designated as total protein extract. Protein concentration of each lysate was determined by the method of Markwell ((1978) A modification of the Lowry procedure to simplify protein determination in membrane and lipoprotein samples. *Anal Biochem* 87(1), 206-10) in the presence of SDS, using BSA as a standard.

SDS-PAGE and immunodetection. Cell lysates (30 μg per lane) were mixed with sample buffer (125 mM Tris/HCl, pH6.8; 4% SDS, 20 mM DTT, 0.05% bromophenol blue, 20% glycerol) and boiled for 2 min. Proteins were separated by SDS-10% polyacrylamide gel according to the method of Schägger and von Jagow ((1987) Tricine-sodium dodecyl sulfate-polyacrylamide gel electrophoresis for the separation of proteins in the range from 1 to 100 kDa. *Analytical Biochemistry* 166(2), 368-79). Electroblotting was performed using a semi-dry transfer system (Hoefer Semiphor unit) onto Immobilon-P membranes (PVDF, Millipore). The transfer was performed in a buffer containing 10 mM CAPS (pH11), 10% (v/v) methanol for 30 min at 2.5 mA/cm$^2$ of gel surface area. Once the electrotransfer was complete, the blots were stained with 0.5% Ponceau-S red to assess the quality of the transfer and washed with Milli-Q®-grade water. The blots were blocked overnight at 4° C. with 5% nonfat milk powder in TBST (150 mM NaCl, 10 mM Tris/HCl pH8, 0.05% Tween-20) (Harlow & Lane, supra) and then incubated with anti-GumB (1:3000) or anti-GumC (1:5000) antibodies in 3% nonfat milk powder in TBST at room temperature for 3 h. Alkaline phosphatase-conjugated goat anti-mouse IgG or anti-rabbit IgG (Sigma) were used for detection, respectively, as described by the manufacturer. The blots were washed three times with TBST and were developed in a solution containing nitroblue tetrazolium-5-bromo-4-chloro-3-indolylphosphate (NBT/BCIP, Promega). Commercial protein markers MW-SDS-70L (Sigma) were used to calibrate SDS-PAGE.

Blot quantification. The intensities of GumB and GumC protein bands were determined by scanning the NBT/BCIP developed filters with a UVP Densitometer (Ultra Violet Products) and quantified with GelWorks 1D Analysis software (NonLinear Dynamics Ltd). Each filter contained a reference lane of a PRM-1(pBBR-prom) extract to establish the level of chromosomally encoded GumB and GumC in the wild type cells. Relative amounts of GumB and GumC were observed. See FIGS. 2A and 2B.

Example 6

Procedure—Molecular Length or Weight Determination Using Atomic Force Microscopy The direct visualization technique called Atomic force Microscopy (AFM) or Scanning Probe Microscope (SPM) was used to image the lengths of xanthan molecules from *X. campestris* strains with (XWCM1/pBBR5-BC) and without (XWCM1) multiple copies of gumB and gumC. The procedure used to perform AFM is detailed below. We observed that the average molecular contour length of xanthan molecules produced by a strain with multiple copies of gumB and gumC was much longer than that of the parental strain.

A 0.1 wt % of gum solution was prepared by mixing 0.1 g of gum in 100 gram distilled water for ~3 hours. A 1-ppm stock solution was prepared by diluting 20 μl of the 0.1 wt % solution into a 20 g 0.1 M ammonium acetate solution. 20 μl of the 1 ppm stock solution was sprayed onto freshly cleaved mica disc(s) (~1 cm$^2$). These mica sample disc(s) were then placed in a heated (~60° C.) vacuum chamber for ~ one hour to remove excess water. The dried mica disc(s) were then scanned using the Tapping Mode of the AFM. The molecular contour length of all AFM images was measured with the software provided by Digital Instruments.

Contour lengths of population of xanthan molecules were measured. The results of this study are summarized in Table 4. (Molecules in each size class are less than or equal to the length indicated; the number of molecules indicated in a size class do not include the molecules counted in a smaller size class.) These results demonstrated that xanthan molecules from *X. campestris* strain with multiple copies of gumB and gumC were significantly larger then xanthan molecules from control strain. The atomic force microscopy (AFM) or scanning probe microscopy (SPM) was performed with a commercial instrument (Nanoscope IIIa, Digital Instruments, Santa Barbara, Calif.) using a silicon nitride cantilever tip.

TABLE 4

AFM Measurement of Xanthan Molecules Contour Length

| | XWCM1 | | | | | XWCM1/pBBR5-BC | | | |
|---|---|---|---|---|---|---|---|---|---|
| Length* | Molecules | Frequency | Distribution | | Length | Molecules | Frequency | Distribution | |
| (μm) | (count) | (%) | No. Avg. | Wt. Avg. | (μm) | (count) | (%) | No. Avg. | Wt. Avg. |
| 0.5 | 225 | 51.5 | ≦3 μm = | ≦3 μm = | 0.5 | 150 | 28.4 | ≦3 μm = | ≦3 μm = |
| 1 | 130 | 29.7 | 99.8% | 98.7% | 1 | 163 | 30.9 | 90.9% | 70.9% |
| 1.5 | 40 | 9.2 | | | 1.5 | 82 | 15.5 | | |
| 2 | 25 | 5.7 | | | 2 | 44 | 8.3 | | |
| 2.5 | 13 | 3.0 | | | 2.5 | 29 | 5.5 | | |
| 3 | 3 | 0.7 | | | 3 | 12 | 2.3 | | |
| 3.5 | 0 | 0.0 | >3 μm = | >3 μm = | 3.5 | 12 | 2.3 | >3 μm = | >3 μm = |
| 4 | 0 | 0.0 | 0.2% | 1.3% | 4 | 13 | 2.5 | 9.1% | 29.1% |
| 4.5 | 0 | 0.0 | | | 4.5 | 7 | 1.3 | | |
| 5 | 1 | 0.2 | | | 5 | 4 | 0.8 | | |
| 5.5 | 0 | 0.0 | | | 5.5 | 4 | 0.8 | | |
| 6 | 0 | 0.0 | | | 6 | 0 | 0.0 | | |
| 6.5 | 0 | 0.0 | | | 6.5 | 3 | 0.6 | | |
| 7 | 0 | 0.0 | | | 7 | 2 | 0.4 | | |
| 7.5 | 0 | 0.0 | | | 7.5 | 0 | 0.0 | | |
| 8 | 0 | 0.0 | | | 8 | 0 | 0.0 | | |
| 8.5 | 0 | 0.0 | | | 8.5 | 1 | 0.2 | | |
| 9 | 0 | 0.0 | | | 9 | 1 | 0.2 | | |
| 9.5 | 0 | 0.0 | | | 9.5 | 1 | 0.2 | | |
| 10 | 0 | 0.0 | | | 10 | 0 | 0.0 | | |
| Total | 437 | | | | Total | 528 | | | |

Example 7

Evaluation of Seawater Viscosity

Xanthan produced by strain XWCM-1/pBBR5-BC was evaluated for seawater viscosity (SWV), compared to a commercial xanthan product (Xanvis™). Typical SWV for Xanvis™ xanthan product is in the range of 18 to 22.

Seawater viscosity was determined using the following procedure. Seawater solution was prepared by dissolving 41.95 g of sea salt (ASTM D1141-52, from Lake Products Co., Inc. Maryland Heights, Mo.) in 1 liter deionized water.

300 ml of seawater solution was transferred to a mixing cup that was attached to a Hamilton-Beach 936-2 mixer (Hamilton-Beach Div., Washington, D.C.). The mixer speed control was set to low and a single fluted disk attached to the mixing shaft. At the low speed setting, the mixer shaft rotates at approximately 4,000-6,000 rpm. 0.86 g of biogum product was slowly added over 15-30 seconds to the mixing cup and allowed to mix for 5 minutes. The mixer speed control was set to high (11,000±1,000 rpm) and the test solution was allowed to mix for approximately 5 minutes. The mixture was allowed to mix for a total of 45 minutes, starting from time of biogum product addition. At the end of the 45 minutes mixing time, 2-3 drops of Bara Defoam (NL Baroid/NL industries, Inc., Houston, Tex.) was added and stirring was continued for an additional 30 seconds.

The mixing cup was removed from the mixer and immersed in chilled water to lower the fluid's temperature to 25±0.5° C. In order to insure a homogeneous solution, the solution was re-mixed after cooling for 5 seconds at 11,000±1,000 rpm. The solution was transferred from the mixing cup to 400 ml Pyrex beaker and Fann viscosity (Fann Viscometer, Model 35A) was measured. This was accomplished by mixing at low speed (about 3 rpm). The reading was allowed to stabilize and then the shear stress value was read from dial and recorded as the SWV value at 3 rpm.

TABLE 5

Quality of XWCM-1/pBBR5-BC xanthan and Xanvis™ xanthan

| Sample | SWV DR[a] |
|---|---|
| XWCM-1/pBBR5-BC | 29 |
|  | 30 |
| Xanvis ™ xanthan | 22 |

[a]dial reading

REFERENCES

1. Kidby, D., Sandford, P., Herman, A., and Cadmus, M. (1977) Maintenance procedures for the curtailment of genetic instability: *Xanthomonas campestris* NRRL B-1459. *Applied and Environmental Microbiology* 33(4), 840-5
2. Ditta, G., Schmidhauser, T., Yakobson, E., Lu, P., Liang, X. W., Finlay, D. R., Guiney, D., and Helinski, D. R. (1985) Plasmids related to the broad host range vector, pRK290, useful for gene cloning and for monitoring gene expression. *Plasmid* 13(2), 149-53
3. Simon, R., Priefer U. and Puhler A. (1983) A broad host range mobilization system for in vivo genetic engineering: transposon mutagenesis in Gram-negative bacteria. *Biotechnology* 1, 784-791
4. Harding, N. E., Cleary, J. M., Cabanas, D. K., Rosen, I. G., and Kang, K. S. (1987) Genetic and physical analyses of a cluster of genes essential for xanthan gumBiosynthesis in *Xanthomonas campestris*. *J Bacteriol* 169(6), 2854-61.
5. Katzen, F., Becker, A., Zorreguieta, A., Puhler, A., and Ielpi, L. (1996) Promoter analysis of the *Xanthomonas campestris* pv. *campestris* gum operon directing biosynthesis of the xanthan polysaccharide. *J Bacteriol* 178(14), 4313-8.
6. Capage, M. R., D. H. Doherty, M. R. Betlach, and R. W. Vanderslice. (1987) Recombinant-DNA mediated production of xanthan gum. International patent WO87/05938.
7. Becker, A., Niehaus, K., and Puhler, A. (1995) Low-molecular-weight succinoglycan is predominantly produced by *Rhizobium meliloti* strains carrying a mutated ExoP protein characterized by a periplasmic N-terminal domain and a missing C-terminal domain. *Molecular Microbiology* 16(2), 191-203
8. Schafer, A., Tauch, A., Jager, W., Kalinowski, J., Thierbach, G., and Puhler, A. (1994) Small mobilizable multi-purpose cloning vectors derived from the *Escherichia coli* plasmids pK18 and pK19: selection of defined deletions in the chromosome of *Corynebacterium glutamicum*. *Gene* 145(1), 69-73
9. Yanisch_Perron, C., Vieira, J., and Messing, J. (1985) Improved M13 phage cloning vectors and host strains: nucleotide sequences of the M13 mp18 and pUC19 vectors. *Gene* 33(1), 103-19
10. Kovach, M. E., Elzer, P. H., Hill, D. S., Robertson, G. T., Farris, M. A., Roop, R. M., and Peterson, K. M. (1995) Four new derivatives of the broad-host-range cloning vector pBBR1MCS, carrying different antibiotic-resistance cassettes. *Gene* 166(1), 175-6
11. Harding, N. E., Cleary, J. M., Cabanas, D. K., Rosen, I. G., and Kang, K. S. (1987) Genetic and physical analyses of a cluster of genes essential for xanthan gumBiosynthesis in *Xanthomonas campestris*. *Journal of Bacteriology* 169(6),
12. Harding N. E., R. S., Raimondi A., Cleary J. M and Telpi L. (1993) Identification, genetic and biochemical analysis of genes involved in synthesis sugar nucleotide precursors of xanthan gum. *J. Gen. Microbiol.* 139, 447-457
13. Sambrook, J., and Russell, D. W. (2001) *Molecular cloning: a laboratory manual*, 3rd Ed., Cold Spring Harbor, N.Y. Cold Spring Harbor Laboratory Press, 2001.

We claim:

1. An unpasteurized xanthan composition from a recombinant *Xanthomonas campestris* culture having multiple copies of gumB and gumC, wherein said composition has an intrinsic viscosity which is at least 20% greater than xanthan from a corresponding strain of *Xanthomonas campestris* not having multiple copies of gumB and gumC.

2. The unpasteurized xanthan composition of claim 1 which has an intrinsic viscosity which is at least 25% greater than xanthan from the corresponding strain.

3. The unpasteurized xanthan composition of claim 1 which has an intrinsic viscosity which is at least 30% greater than xanthan from the corresponding strain.

4. A xanthan composition from a recombinant *Xanthomonas campestris* culture having multiple copies of gumB and gumC, comprising a population of xanthan molecules having a range of molecular lengths, wherein at least 1% of the population has a length of at least 3 μm as measured by atomic force microscopy.

5. An unpasteurized xanthan composition from a recombinant *Xanthomonas campestris* culture having multiple copies of gumB and gumC, wherein said composition has a seawater viscosity which is at least 10% greater than xanthan from a corresponding strain of *Xanthomonas campestris* not having multiple copies of gumB and gumC.

6. The xanthan composition of claim 5 which has a seawater viscosity of DR>25 when the seawater viscosity is measured in a solution of 41.95 g of sea salt per 1 liter deionized water and at a concentration of 0.86 g xanthan per liter.

7. The xanthan composition of claim 5 which has a seawater viscosity which is at least 15% greater than xanthan from the corresponding strain.

* * * * *